United States Patent
Nomura et al.

(10) Patent No.: US 7,232,619 B2
(45) Date of Patent: Jun. 19, 2007

(54) PYRENE DERIVATIVE, LIGHT EMITTING ELEMENT, AND LIGHT EMITTING DEVICE

(75) Inventors: Ryoji Nomura, Kanagawa (JP); Takako Takasu, Kanagawa (JP); Hiroko Abe, Tokyo (JP); Atsushi Tokuda, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

(21) Appl. No.: 10/954,341

(22) Filed: Oct. 1, 2004

(65) Prior Publication Data

US 2005/0079385 A1    Apr. 14, 2005

(30) Foreign Application Priority Data

Oct. 3, 2003    (JP) .............................. 2003-345195

(51) Int. Cl.
*H05B 33/14* (2006.01)
*C09K 11/06* (2006.01)

(52) U.S. Cl. ...................... 428/690; 428/917; 313/504; 252/301.16

(58) Field of Classification Search ................ 428/690, 428/917; 313/504, 506; 252/301.16; 257/40
See application file for complete search history.

(56) References Cited

U.S. PATENT DOCUMENTS 5,707,779 A * 1/1998 Naito ...................... 430/270.1
6,750,472 B2 * 6/2004 Suzuki et al. .................. 257/40
7,060,370 B2 * 6/2006 Kinoshita et al. ........... 428/690

FOREIGN PATENT DOCUMENTS

JP       2001-118682       4/2001
JP       2004-166962  *    1/2004

OTHER PUBLICATIONS

W. Sotoyama et al., *45.3: Tetra-Substituted Pyrenes: New Class of Blue Emitter for Organic Light-Emitting Diodes*, SID 03 Digest, pp. 1294-1297 (2003).

* cited by examiner

Primary Examiner—Bruce H. Hess
Assistant Examiner—Camie S. Thompson
(74) Attorney, Agent, or Firm—Eric J. Robinson; Robinson Intellectual Property Law Office, P.C.

(57) ABSTRACT

It is an object of the present invention to provide a pyrene derivative represented by the general formula (1) that is unlikely to crystallize and is superior in quality in the case of forming a film (1)

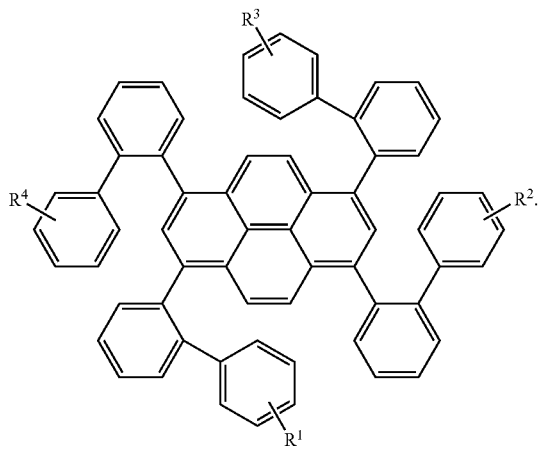

11 Claims, 9 Drawing Sheets

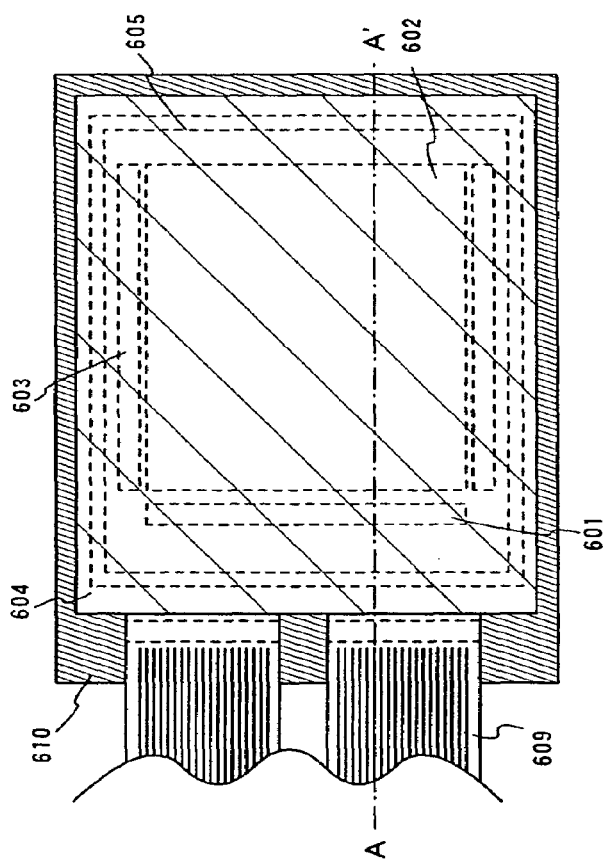
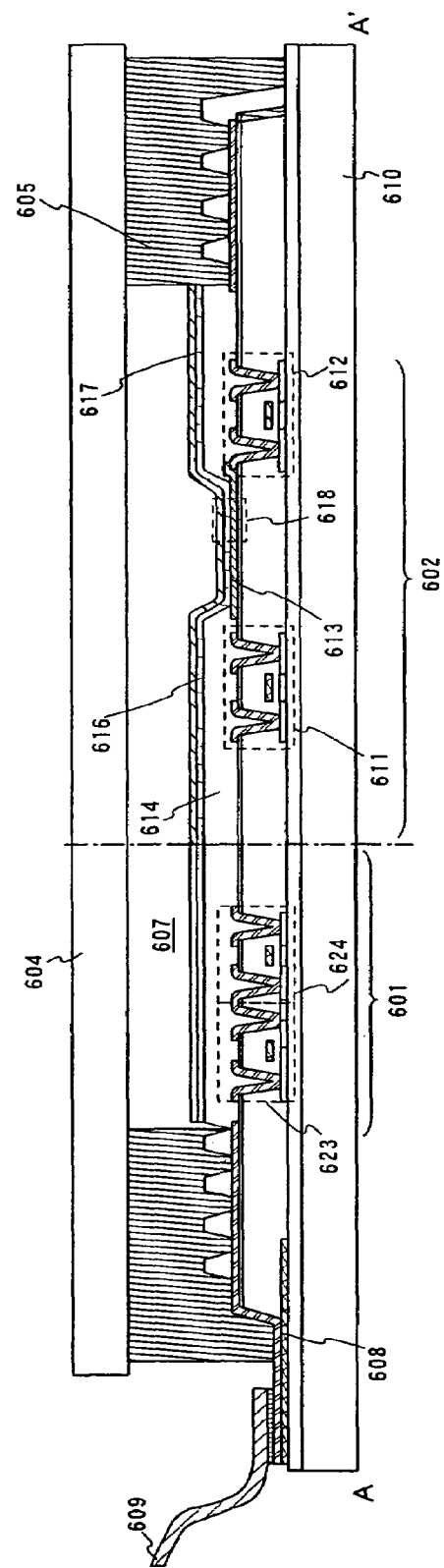
Fig. 8A
Fig. 8B

PYRENE DERIVATIVE, LIGHT EMITTING ELEMENT, AND LIGHT EMITTING DEVICE

BACKGROUND OF THE INVENTION

1. Field of the Invention

The present invention relates to a pyrene derivative that emits light efficiently, has great heat resistance, permits an uniform film to be formed, and is morphologically stable, and further relates to a light-emitting element that has an anode, a cathode, and a layer including an organic compound from which luminescence can be obtained by applying an electric field (hereinafter, referred to as "a layer including a luminescent layer").

2. Description of the Related Art

Organic compounds include more varied material kinds of materials in comparison with inorganic compounds, and have a possibility that a material that has various functions can be synthesized by an appropriate molecular design. Also, they have features that a molded article such as a film is flexible and excellent workability is provided by polymerization. Based on these advantages, photonics and electronics utilizing functional organic materials have been attracting attention recently.

For example, examples of a photoelectric device utilizing an organic semiconductor material as a functional organic material include a solar cell and a light-emitting device (also referred to as an organic electroluminescent device), which are devices utilizing an electric property (carrier transporting property) and an optical property (light absorption or light emission) of the organic semiconductor material, and, among them, the light-emitting device has been showing remarkable progresses.

The light-emitting device has a light-emitting element interposing a layer including a luminescent material between a pair of electrodes (an anode and a cathode), which is said to have the light emission mechanism that a hole injected from the anode and an electron injected from the cathode are recombined in the luminescence center of the layer including the luminescent material to form an excited molecule in an excited state when a voltage is applied between the both electrodes and energy is released to emit light while the excited molecule moves back toward the ground state. As the excited state, a singlet excited state and a triplet excited state are known, and luminescence is said to be possible through any of the singlet excited state and the triplet excited state.

In order to manufacture a full-color display by using the light-emitting element, it is necessary to arrange pixels that emit light of three primary colors of red, green, and blue. As a method for that purpose, there are various applicable methods. However, blue luminescence is indispensable in any method, and it is desired to provide a blue light-emitting element that is high in luminance, efficiency, and color purity.

Meanwhile, as a conventional blue light-emitting element, a light-emitting element using 1,3,6,8-tetraphenylpyrene or a derivative thereof as a luminescent material is known (refer to Patent Document 1 and Non-Patent Document1, for example). However, since a thin film of the luminescent material is likely to undergo crystallization, there is a problem that it is difficult to keep the film morphologically uniform and obtain stable light emission for a long stretch of time. Further, the luminous efficiency is insufficient.

(Patent Document 1)
Japanese Patent Laid-Open No. 2001-118682

(Non-Patent Document 1)
Wataru Sotoyama, et al., 2003 SID International Symposium Digest of Technical Papers, Vol. 34, 1294–1297 (2003)

SUMMARY OF THE INVENTION

It is an object of the present invention to provide a pyrene derivative that permits an uniform film to be formed, and that is unlikely to undergo crystallization and morphologically stable. In addition, it is an object of the present invention to provide a light-emitting element from which stable light emission can be obtained for a long stretch of time and a light-emitting device using the light-emitting element.

A lot of earnest studies of the inventors have finally found out that a pyrene derivative represented by the following general formula (1) emits light efficiently and is unlikely to crystallize. Accordingly, an aspect of the present invention is a pyrene derivative represented by the following general formula (1).

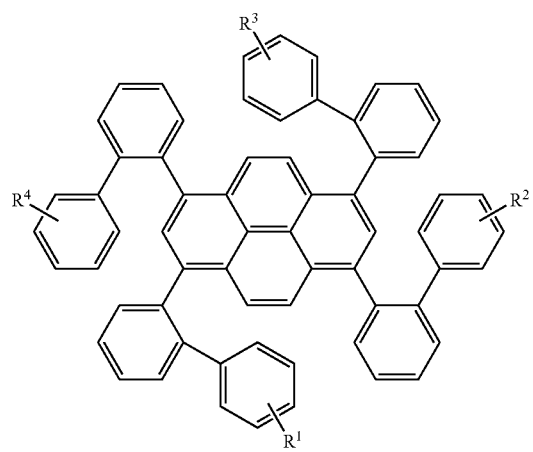

(1)

(where $R_1$ to $R_4$ may be identical or different, and are individually any substituent selected form the group consisting of an alkyl group having 1 to 6 carbon atoms, an alkoxyl group having 1 to 6 carbon atoms, an aryl group, a diarylamino group, and a silyl group having one or more alkyl groups or one or more aryl groups.)

By using the pyrene derivative mentioned above, a light-emitting element from which stable light emission can be obtained efficiently for a long stretch of time can be manufactured. Accordingly, another aspect of the present invention is a light-emitting element including the pyrene derivative mentioned above. Since the pyrene derivative according to the present invention shows high-efficiency luminescence, it is preferable that the pyrene derivative mentioned above is included in a light-emitting layer.

The pyrene derivative according to the present invention permits an uniform film to be formed and is unlikely to undergo crystallization and morphologically stable. Therefore, stable light emission can be obtained for a long stretch of time by using the pyrene derivative according to the present invention for a light-emitting element. In addition, by using the light-emitting element according to the present invention, it becomes possible to obtain a light-emitting device that emits light stably for a long stretch of time.

BRIEF DESCRIPTION OF THE DRAWINGS

In the accompanying drawings:

FIGS. 8A and 8B are diagrams illustrating a light-emitting device; and

DETAILED DESCRIPTION OF THE INVENTION

Figure 1:
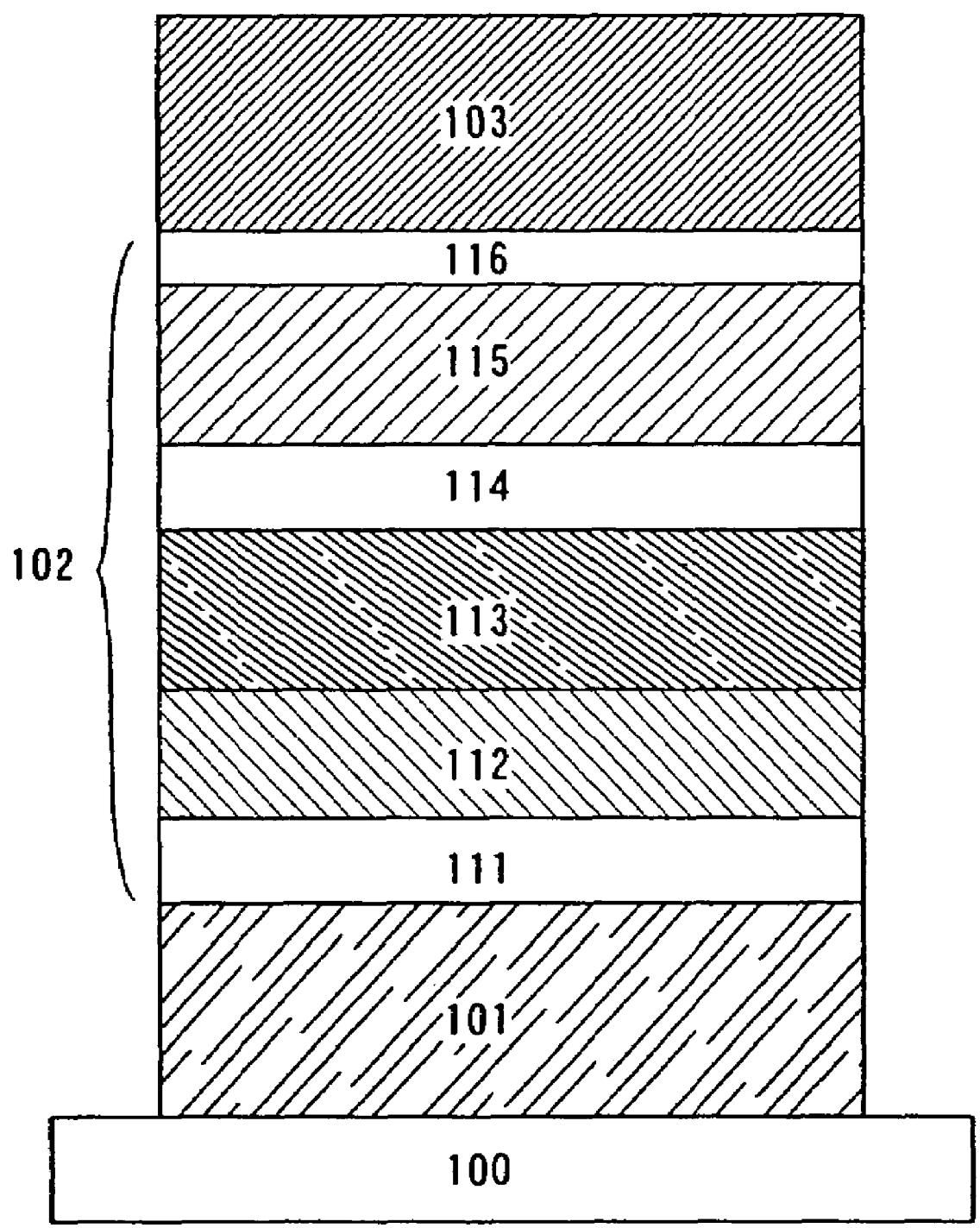
FIG. 1 is a diagram illustrating a structure of a light-emitting element according to the present invention.

Hereinafter, embodiments of the present invention will be described with reference to the drawings. However, the present invention is not limited to the following descriptions, and it is to be understood that various changes and modifications will be apparent to those skilled in the art unless such changes and modifications depart from the scope of the present invention. Therefore, the invention is not to be considered limited to what is described in the following embodiments.

(Embodiment 1)

A pyrene derivative according to the present invention has a structure represented by the above-mentioned general formula (1). Specific examples of $R_1$ to $R_4$ include alkyl groups such as a methyl group, an ethyl group, an isopropyl group, and a cyclohexyl group, alkoxyl groups such as a methoxy group, an isopropoxy group, and a hexyloxy group, aryl groups such as a phenyl group, a naphthyl group, and an anthryl group, diarylamino groups such as a diphenylamino group and a carbazolyl group, and a silyl group having one or more alkyl groups or one or more aryl groups.

In addition, by appropriately changing the structures of $R_1$ to $R_4$ in the general formula (1), pyrene derivatives represented by the following structure formulas (2) to (12) can be formed, for example. However, the present invention is not to be considered limited to these.

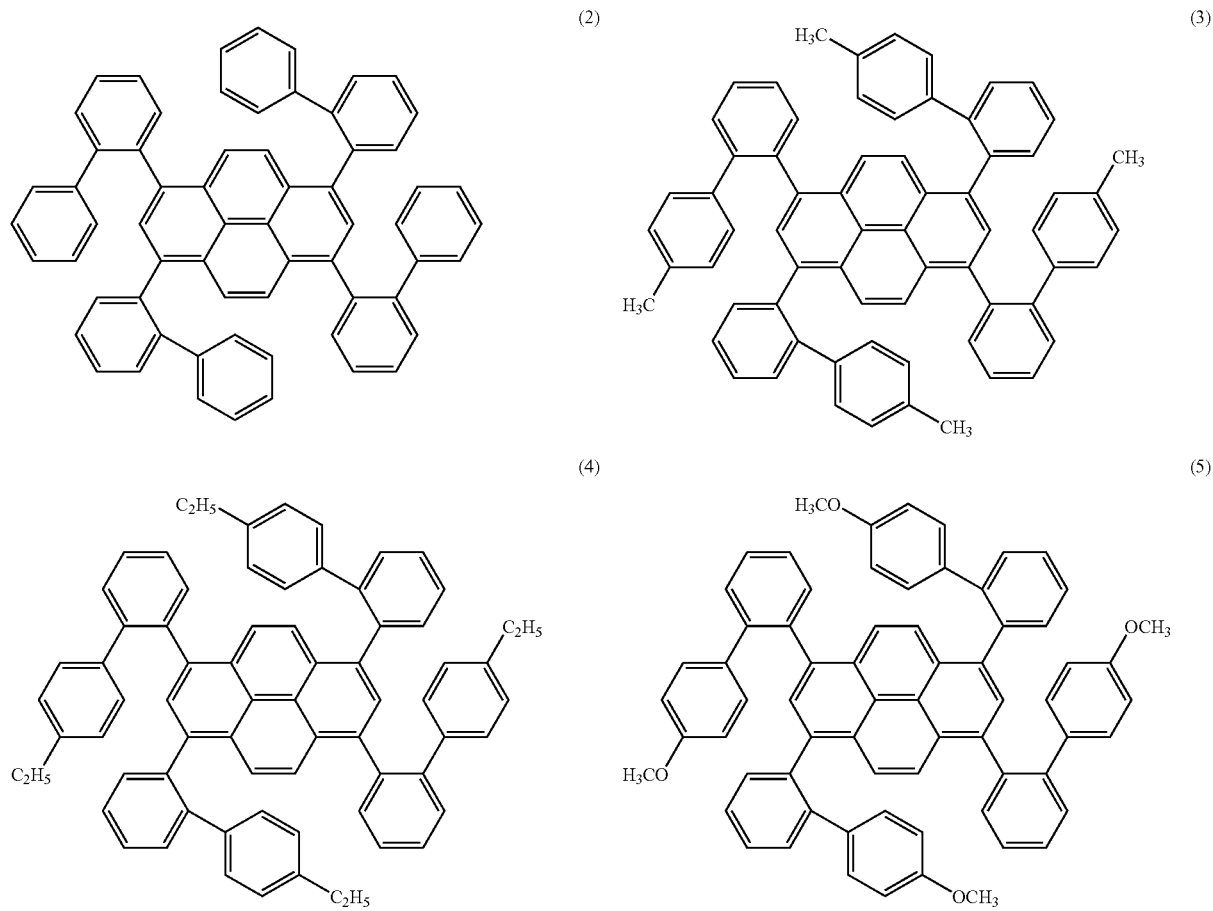

(6)
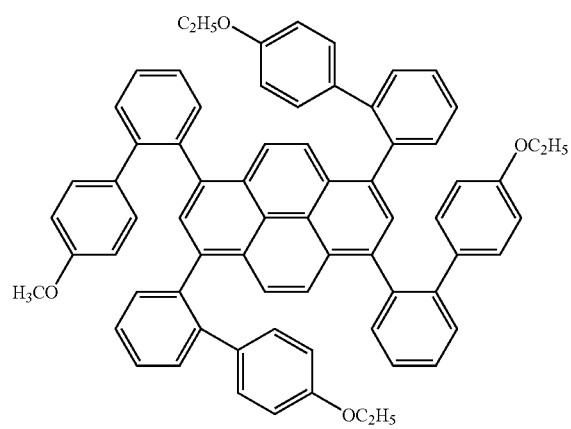
(7)
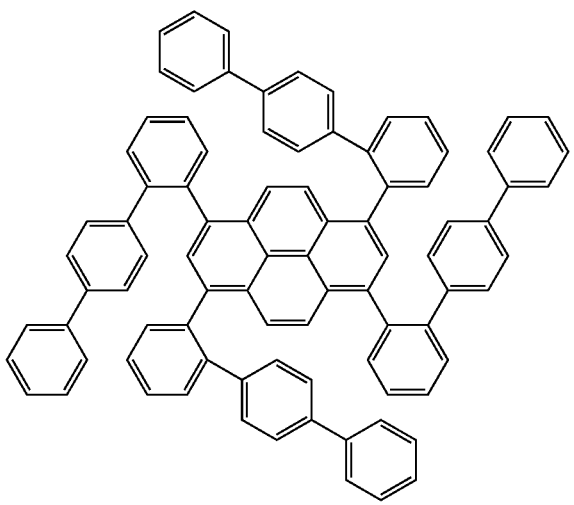
(8)
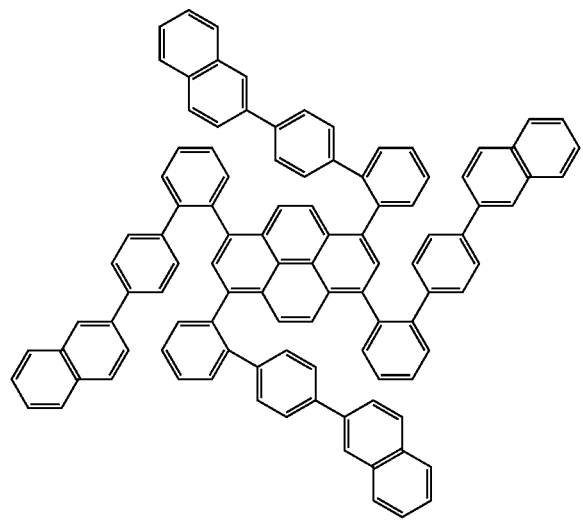
(9)
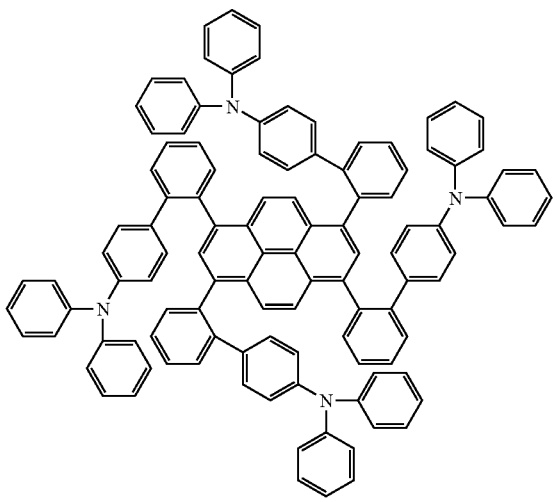

(10)
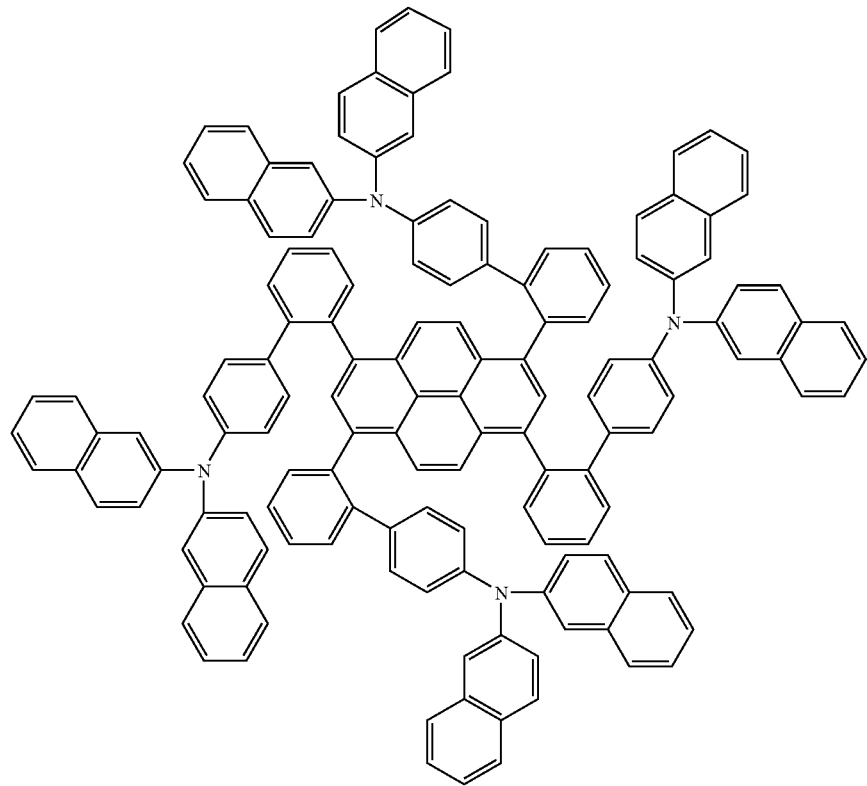
(11)
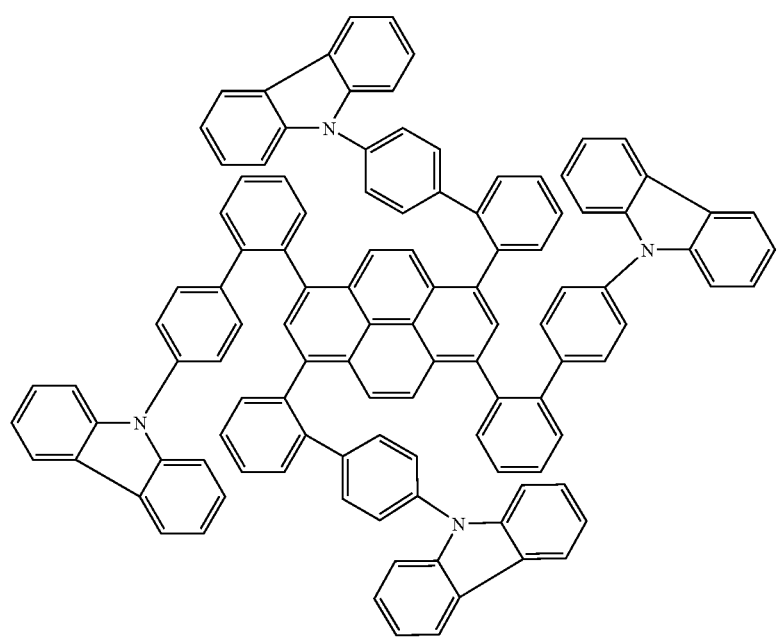

-continued (12)

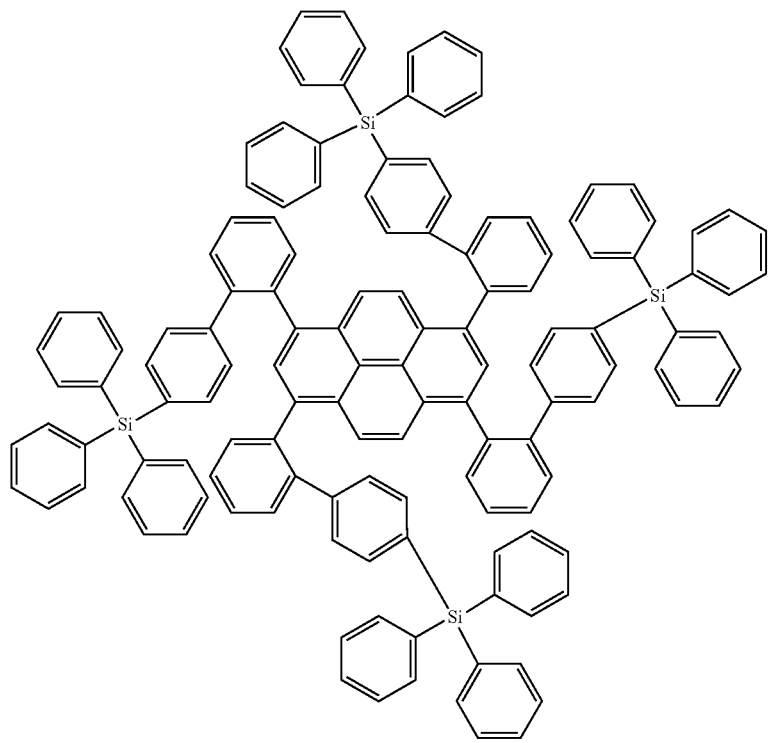

The pyrene derivative according to the present invention is large in molecular weight and has a three-dimensional structure since a phenyl group is bonded at the ortho position of a phenyl group bonded at each of 1-, 3-, 6-, and 8-positions of a pyrene. Accordingly, the pyrene derivative according to the present invention has not only great heat resistance but also a property of permitting an uniform film to be formed and a property of being unlikely to undergo crystallization, that is, being morphologically stable.

In addition, the pyrene derivative according to the present invention has a property of emitting light efficiently.

Various reactions can be applied to a synthesis method of the pyrene derivative according to the present invention. As a synthesis scheme of the pyrene derivative represented by the above-mentioned structure formula (2), there is the following method. However, the synthesis method of the pyrene derivative according to the present invention is not to be considered limited to this.

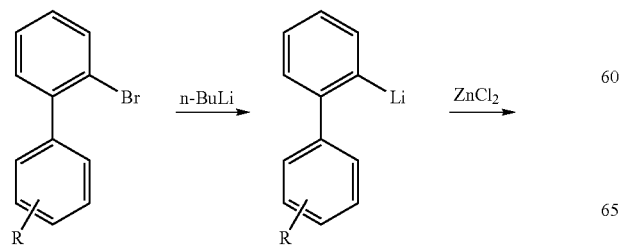

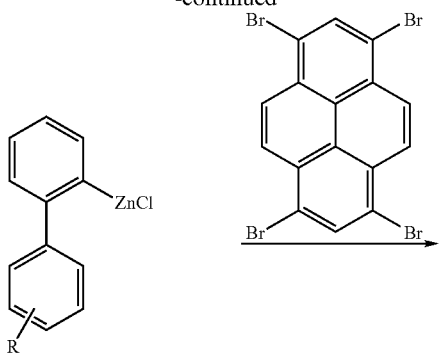

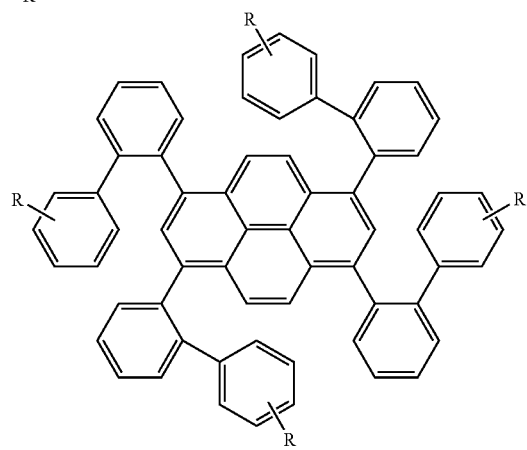

(Embodiment 2)

In the present embodiment, a light-emitting element using the pyrene derivative shown in Embodiment 1 will be described.

The structure of the light-emitting element according to the present invention is not particularly limited, which can be selected appropriately for any purpose. Basically, the structure has a layer including a luminescent material between a pair of electrodes (an anode and a cathode), which is formed by appropriately combining layers such as a hole injecting layer, a hole transporting layer, a light-emitting layer, a hole blocking layer, an electron transporting layer, and an electron injecting layer. For example, a light-emitting element that has a structure such as an anode/a hole injecting layer/a light-emitting layer/an electron transporting layer/a cathode, an anode/a hole injecting layer/a hole transporting layer/a light-emitting layer/an electron transporting layer/a cathode, an anode/a hole injecting layer/a hole transporting layer/a light-emitting layer/an electron transporting layer/an electron injecting layer/a cathode, an anode/a hole injecting layer/a hole transporting layer/a light-emitting layer/a hole blocking layer/an electron transporting layer/a cathode, or an anode/a hole injecting layer/a hole transporting layer/a light-emitting layer/a hole blocking layer/an electron transporting layer/an electron injecting layer a cathode, is included. In addition, the pyrene derivative according to the present invention is included in the light-emitting element according to the present invention, which may be included in any of a light-emitting layer, a hole transporting layer, a hole injecting layer, an electron transporting layer, and an electron injecting layer. Either the anode or the cathode may be laminated first.

Additionally, it is preferable that the light-emitting element according to the present invention is supported by a substrate. The substrate is not particularly limited, and a substrate that is used for a conventional light-emitting element, for example, a substrate including a material such as glass, quartz, or transparent plastic can be used.

As an anode material for the light-emitting element according to the present invention, it is preferable to use a metal, an alloy, an electrically conductive compound, or a mixture thereof, which has a large work function (a work function of 4.0 eV or more). As a specific example of the anode material, a metal such as gold (Au), platinum (Pt), nickel (Ni), tungsten (W), chromium (Cr), molybdenum (Mo), iron (Fe), cobalt (Co), copper (Cu), or palladium (Pd), and a nitride of a metal material such as TiN can be used in addition to indium tin oxide (hereinafter, referred to as ITO) and indium oxide including zinc oxide (ZnO) at 2 to 20%.

On the other hand, as a cathode material, it is preferable to use a metal, an alloy, an electrically conductive compound, or a mixture of these, which has a small work function (a work function of 3.8 eV or less). As a specific example of the cathode material, an alkali metal (such as Li, Na, K, or Cs), an alkali earth metal (such as Mg or Ca), gold, silver, lead, aluminum, an alloy or mixed metal of aluminum and lithium, and an alloy or mixed metal of magnesium and silver can be used. Further, between the cathode including the metal mentioned above and an organic layer, a metal oxide or a metal halide may be used as an electron injecting layer. As specific examples of the electron injecting layer, metal oxides such as lithium oxide ($Li_2O$), magnesium oxide (MgO), and aluminum oxide ($Al_2O_3$), and metal halides such as lithium fluoride (LiF), magnesium fluoride ($MgF_2$), strontium fluoride ($SrF_2$) can be used.

A thin film including the anode material and a thin film including the cathode material are formed by a method such as evaporation or sputtering to form the anode and the cathode respectively, which preferably have a film thickness of 10 to 500 nm.

In the light-emitting element according to the present invention, light generated by recombination of carriers in the layer including the luminescent material is emitted from one or both of the anode and the cathode to the outside. In other words, the anode is formed to include light-transmitting material in the case where light is emitted from the anode while the cathode is formed to include a light-transmitting material in the case where light is emitted from the cathode.

For the layer including the luminescent material, known materials can be used, and any of low molecular weight materials and high molecular weight materials can be used. The pyrene derivative according to the present invention is included in the layer including the luminescent material. The materials for forming the layer including the luminescent material includes not only organic compounds but also an inorganic compound included in a portion of the layer including the luminescent material.

The layer including the luminescent material is formed by appropriately combining layers such as a hole injecting layer including a hole injecting material, a hole transporting layer including a hole transporting material, a light-emitting layer including a luminescent material, a hole blocking layer including a hole blocking material, an electron transporting layer including an electron transporting material, and an electron injecting layer including an electron injecting material, which may have a single layer or have a laminated structure including a plurality of layers.

In the present invention, in the case of using the pyrene derivative for the light-emitting layer, the layer including the luminescent material can be formed by appropriately combining layers in addition to the light-emitting layer. In other words, the layer including the luminescent material can have a laminated structure by combining layers such as the hole injecting layer, the hole transporting layer, the hole blocking layer, the electron transporting layer, and the electron injecting layer as appropriate in addition to the light-emitting layer. Here are specific materials to be used in this case.

As the hole injecting material, porphyrin-based compounds are efficient among organic compounds. For example, phthalocyanine (hereinafter, referred to as $H_2$-Pc) and copper phthalocyanine (hereinafter, referred to as Cu-Pc) can be used. In addition, a material of a chemically doped conductive polymer such as polyethylene dioxythiophene (hereinafter, referred to as PEDOT) doped with polystyrene sulfonate (hereinafter, referred to as PSS) can be used.

As the hole transporting material, an aromatic amine-based compound (that is, a compound that has a benzene ring-nitrogen bond) is preferred. As materials that are widely used, for example, in addition to N,N'-bis(3-methylphenyl)-N,N'-diphenyl-[1,1'-biphenyl]-4,4'-diamine (hereinafter, referred to as TPD), derivatives thereof such as 4,4'-bis[N-(1-naphthyl)-N-phenyl-amino]-biphenyl (hereinafter, referred to as α-NPD) and starburst aromatic amine compounds such as 4,4',4"-tris(N-carbazolyl)-triphenylamine (hereinafter, referred to as TCTA), 4,4',4"-tris(N,N-diphenyl-amino)-triphenylamine (hereinafter, referred to as TDATA), and 4,4',4"-tris[N-(3-methylphenyl)-N-phenyl-amino]-triphenylamine (hereinafter, referred to as MTDATA) are included.

As the electron transporting material, a metal complex that has a quinoline moiety or a benzoquinoline moiety such as tris(8-quinolinolato)aluminum (hereinafter, referred to as $Alq_3$), tris(4-methyl-8-quinolinolato)aluminum (hereinafter, referred to as Almq₃), or bis (10-hydroxybenzo[h]-quinolinato)beryllium (hereinafter, referred to as BeBq₂), and bis (2-methyl-8-quinolinolato)-(4-hydroxy-biphenylyl)-aluminum (hereinafter, referred to as BAlq) that is a mixed ligand complex are preferred. In addition, there is also a metal complex that has an oxazole-based, thiazole-based, or benzimidazole-based ligand such as bis [2-(2-hydroxyphenyl)-benzoxazolato]zinc (hereinafter, referred to as Zn(BOX)₂), bis[2-(2-hydroxyphenyl)-benzothiazolato]zinc (hereinafter, referred to as Zn(BTZ)₂), or tris-(2-(2'-hydroxyphenyl)-1-phenyl-1H-benzimidazolate)aluminum (hereinafter, referred to as Al(PBI)₃).

In addition to the metal complex, oxadiazole derivatives such as 2-(4-biphenylyl)-5-(4-tert-butylphenyl)-1,3,4-oxadiazole (hereinafter, referred to as PBD) and 1,3-bis[5-(p-tert-butylphenyl)-1,3,4-oxadiazole-2-yl]benzene (hereinafter, referred to as OXD-7), triazole derivatives such as 3-(4-tert-butylphenyl)-4-phenyl-5-(4-biphenylyl)-1,2,4-triazole (hereinafter, referred to as TAZ) and 3-(4-tert-butylphenyl)-4-(4-ethylphenyl)-5-(4-biphenylyl)-1,2,4-triazole (hereinafter, referred to as p-EtTAZ), phenanthroline derivatives such as bathophenanthroline (hereinafter, referred to as BPhen) and bathocuproin (hereinafter, referred to as BCP), and benzimidazole derivatives such as 2,2',2"-(1,3,5-benzenetriyl)tris-[1-phenyl-1H-benzimidazole] (hereinafter, referred to as TPBI), 1,3,5-tris[4-(1-phenyl-1H-benzimidazole-2-yl)phenyl]benzene (hereinafter, referred to as TPBIBB), and 9-phenyl-2,4,5,7-tetrakis(1-phenyl-1H-benzimidazole-2-yl)-carbazole (hereinafter, referred to as PBIC) can be used.

As the hole blocking material, materials such as the above-mentioned BAlq, OXD-7, TAZ, p-EtTAZ, BPhen, and BCP can be used In addition, the pyrene derivative according to the present invention can be used as a host material or guest material of the light-emitting layer.

In the case of using the pyrene derivative as a host material of the light-emitting layer, triplet luminescent materials (phosphorescent materials) such as tris (2-phenylpyridine)iridium (hereinafter, referred to as Ir(ppy)3) and 2,3,7,8,12,13,17,18-octaethyl-21H,23H-porphyrin-platinum (hereinafter, referred to as PtOEP) can be used as a guest material in addition to quinacridone, diethyl quinacridone (DEQ), rubrene, perylene, DPT, Co-6, PMDFB, BTX, ABTX, DCM, and DCJT.

In the case of using the pyrene derivative as a guest material of the light-emitting layer, materials such as TPD, a-NPD, 4,4'-bis (carbazolyl)-biphenyl (hereinafter, referred to as CBP), TCTA, PBD, OXD-7, BCP can be used as a host material.

As described above, a light-emitting element from which stable light emission can be obtained efficiently for a long stretch of time can be manufactured by using the pyrene derivative according to the present invention, which has material properties of emitting light efficiently, having great heat resistance, permitting an uniform film to be formed, and being unlikely to undergo crystallization and morphologically stable.

(Embodiment 3)

In the present embodiment, a light-emitting device according to the present invention will be described.

In the present embodiment, the light-emitting element using the pyrene derivative according to the present invention, which is shown in Embodiment 2, is manufactured over a substrate including a material such as glass, quartz, or transparent plastic. By manufacturing a plurality of light-emitting elements using the pyrene derivative according to the present invention over a substrate, a passive matrix light-emitting device can be manufactured.

Figure 5:
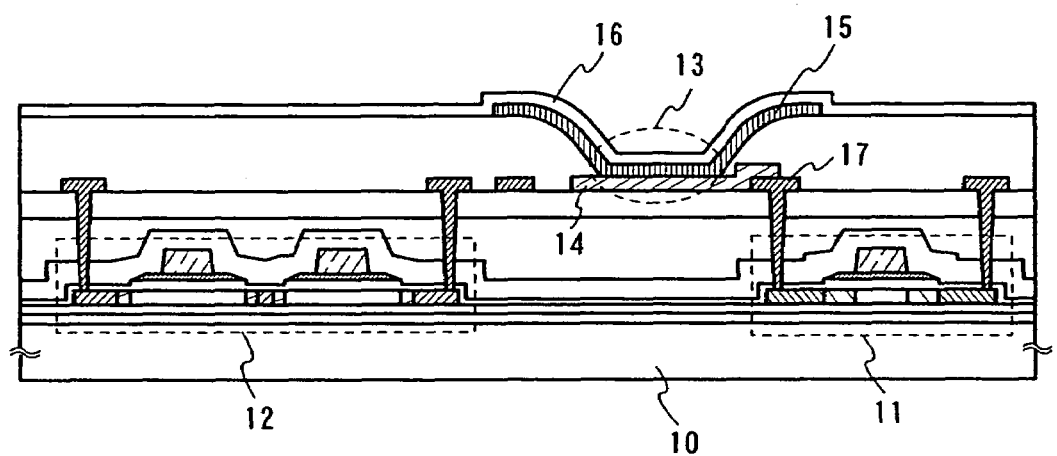
FIG. 5 is a diagram illustrating a light-emitting device.

In addition, other than the substrate including the material such as glass, quartz, or transparent plastic, for example, as shown in FIG. 5, a light-emitting element in contact with a thin film transistor (TFT) array may be manufactured, and in this case, an active matrix light-emitting device where driving of a TFT is controlled by a TFT can be manufactured. In FIG. 5, a TFT 11 and a TFT 12 are formed over a substrate 10, to which a light-emitting element 13 is connected. Specifically, by applying a current from the TFT 11 to a first electrode 14 through a wiring 17, an electric field is applied between the first electrode 14 and a second electrode 16 and a layer 15 including a luminescent material emits light. FIG. 5 shows gates of the staggered TFTs. However, The structures of the TFTs are not particularly limited. For example, a staggered TFT and an inversely staggered TFT may be used. In addition, the degree of crystallinity a semiconductor layer forming the TFT is not particularly limited, either. A crystalline semiconductor layer or an amorphous semiconductor layer may be used to form the TFT.

EXAMPLE 1

In the present example, an example of synthesizing the pyrene derivative represented by the above-mentioned structure formula (2) will be specifically exemplified.

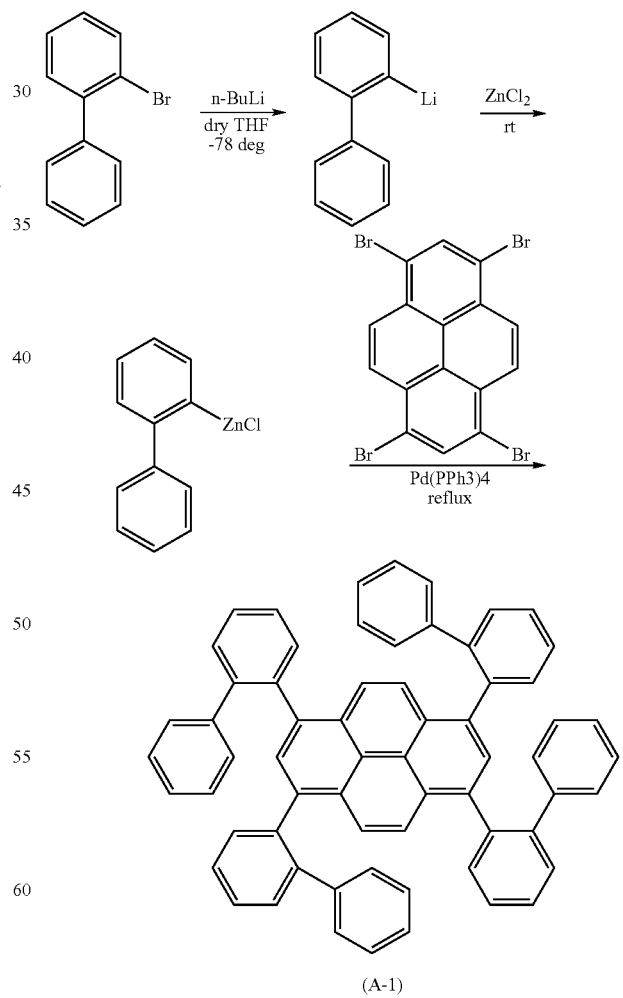

(A-1)

First, in accordance with the above synthesis scheme (A-1), 10.4 g (44.8 mmol) of distilled 2-bromobiphenyl was added to a solution of dried tetrahydrofran (hereinafter, referred to as THF) in an atmosphere of nitrogen, and further, 31 ml of a 1.56 N hexane solution of n-buthyllithium (48 mmol) was dropped at −78° C. After the dropping, stirring was performed at −78° C. for 1 hour. After the stirring, the suspension was added to dried zinc chloride in an atmosphere of nitrogen, and stirring was performed at room temperature for 1 hour After the stirring, 4.64 g (9.0 mmol) of 1,3,6,8-tetrabromopyrene was added, and 517 mg (0.45 mmol) of tetrakis (triphenyl phosphine) palladium was further added. After that, reflux for 24 hours was performed. After the reflux, the solution was condensed to precipitate a solid, and the precipitated solid was washed with 3% hydrochloric acid, water, and ethanol, and further washed with hexane. Finally, the solid was washed with a small amount of THF to obtain 1,3,6,8-tetra-2-(phenyl)phenyl-pyrene (the above structure formula (2); hereinafter, referred to as TBiPy) that is light green powder, where the yield was 48%.

Figure 2:
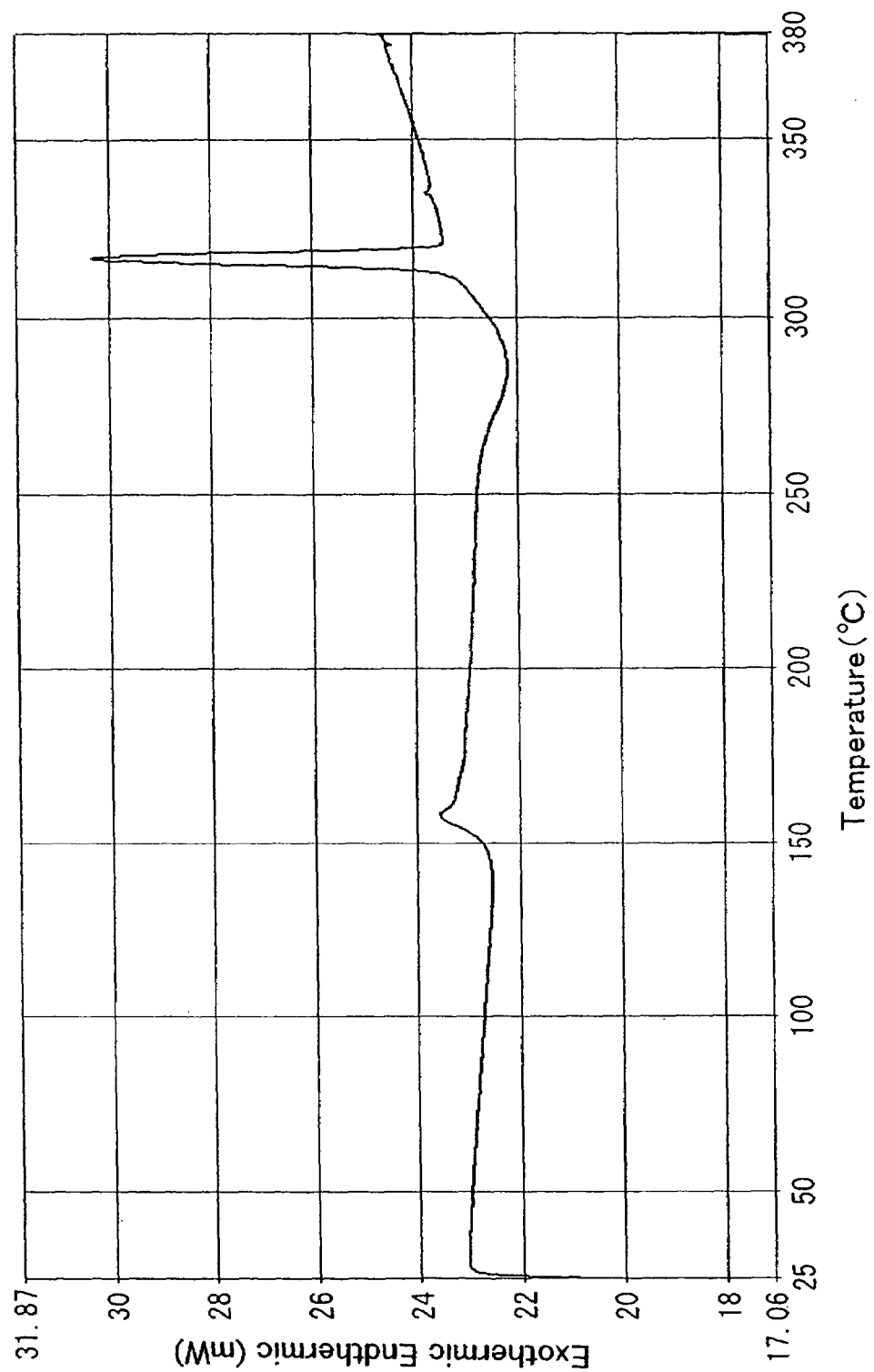
FIG. 2 is a diagram showing a result of a DSC measurement of a pyrene derivative.

It was determined according to a TG-DTA measurement that the thermal decomposition temperature of the obtained TBiPy was 414° C. In addition, FIG. 2 shows a result of a DSC measurement. It is determined from FIG. 2 that glass transition temperature Tg is 148° C., crystallization temperature Tc is 260° C., and melting point Tm is 304° C. As described above, it is determined that the pyrene derivative according to the present invention has the high glass transition temperature, the high melting point, and the high thermal decomposition temperature, hence has great heat resistance. Further, the peak showing the crystallization temperature is not clear in FIG. 2, which suggests that the pyrene derivative is a material that is unlikely to undergo crystallization. When vacuum deposition was used to deposit the pyrene derivative actually, it was possible to form a uniform film.

Figure 3:
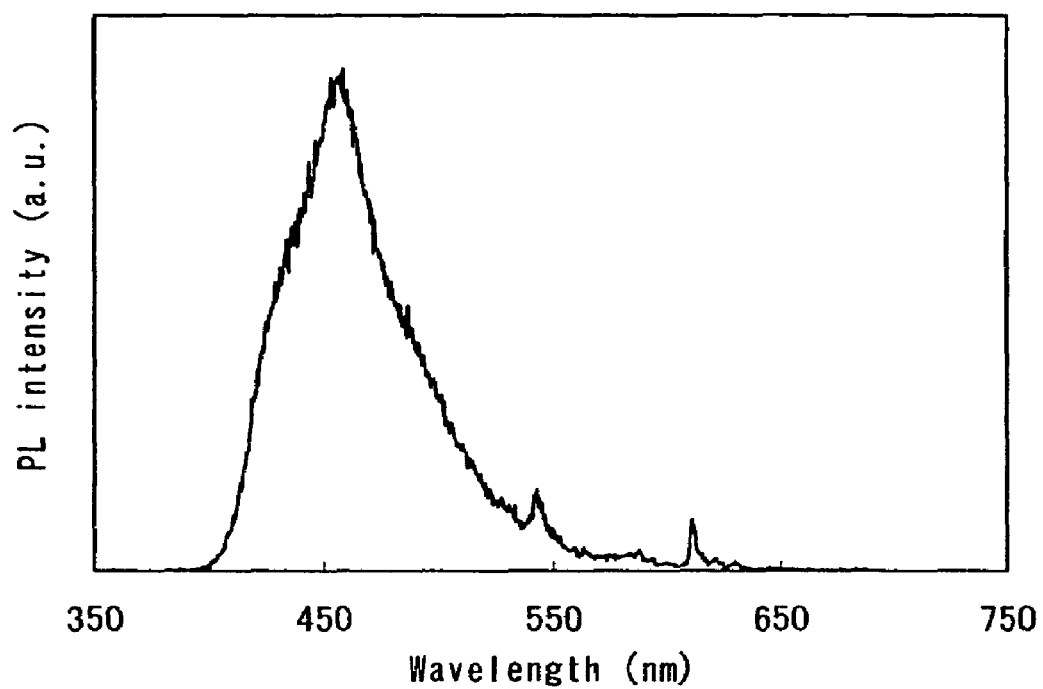
FIG. 3 is a diagram showing a fluorescence spectrum of the pyrene derivative.
Figure 4:
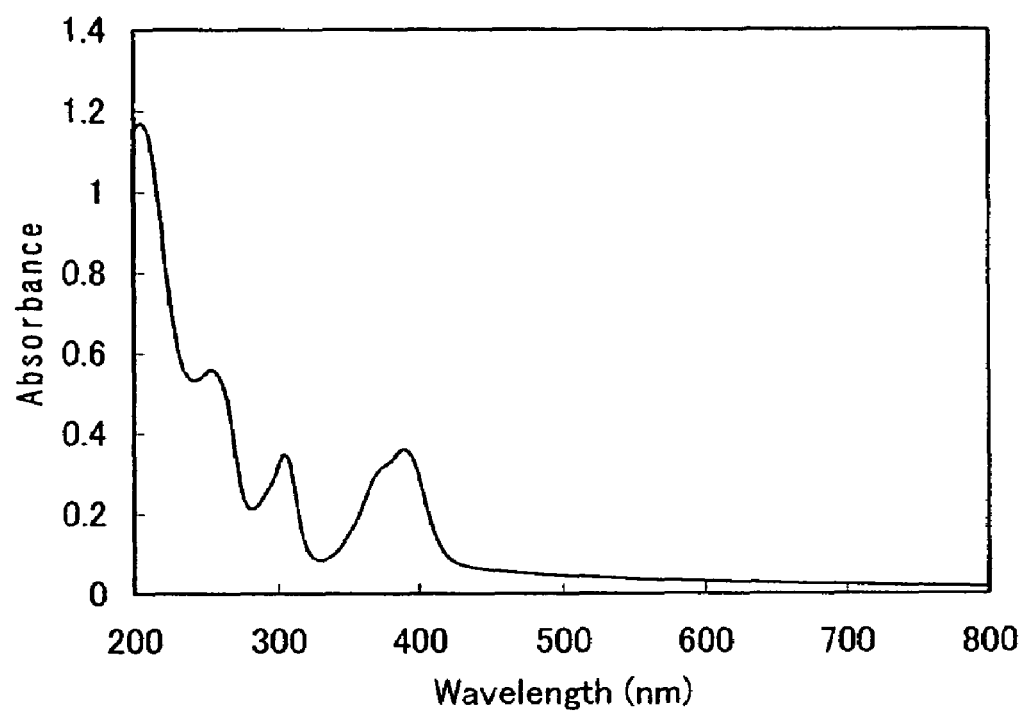
FIG. 4 is a diagram showing an UV-Vis absorption spectrum of the pyrene derivative.

When a fluorescence spectrum of a thin film of the obtained TBiPy was measured, the obtained fluorescence spectrum had a maximum peak at 457 nm with respect to an excitation wavelength (355 nm) (FIG. 3). In addition, when a UV-Vis absorption spectrum of a thin film of the obtained TBiPy was measured, a maximum absorption wavelength of 389 nm was obtained (FIG. 4).

Further, the value of a HOMO level that was measured by using Electron Spectrometer for Chemical Analysis AC-2 (from Riken Keiki Co., Ltd.) is −5.77 eV. In addition, the value of a LUMO level that was estimated by adding the value of an absorption edge of the absorption spectrum (FIG. 4), as an energy gap, to the value of the HOMO level is −2.79 eV.

EXAMPLE 2

In the present example, a case of using a pyrene derivative according to the present invention for a portion of a layer including a luminescent material to manufacture a light-emitting element, specifically, a structure in the case of a pyrene derivative according to the present invention for a light-emitting layer will be described with reference to FIG. 1.

First, a first electrode 101 for a light-emitting element is formed over a substrate 100. In the present example, the first electrode 101 functions as an anode. ITO that is a transparent conductive film is used as a material to form the first electrode 101 with a film thickness of 110 nm by sputtering.

Next, a layer 102 including a luminescent material is formed on the first electrode (anode) 101. The layer 102 including the luminescent material in the present example has a laminated structure including a hole injecting layer 111, a hole transporting layer 112, a light-emitting layer 113, a hole blocking layer 114, an electron transporting layer 115, and an electron injecting layer 116.

The substrate over which the first electrode 101 is formed fixed in a substrate holder of a commercially produced vacuum deposition device with the surface at which the first electrode 101 is formed down, copper phthalocyanine (hereinafter, referred to as Cu-Pc) is put in an evaporation source provided in the vacuum deposition device, and then, the hole injecting layer 111 is formed by evaporation using resistance heating to have a film thickness of 20 nm. As a material for forming the hole injecting layer 111, a known hole injecting material can be used.

Then, a highly hole transporting material is used to form the hole transporting layer 112. As a material for forming the hole transporting layer 112, a known hole transporting material can be used. In the present example, α-NPD is used to form the hole transporting layer 112 with a film thickness of 40 nm in the same way.

Then, the light-emitting layer 113 is formed. In the light-emitting layer 113, a hole and an electron are recombined to generate luminescence (to emit light). In the present example, TBiPy that is a pyrene derivative according to the present invention is used as a material for forming the light-emitting layer 113 to form the light-emitting layer 113 with a film thickness of 30 nm by evaporation.

Then, the hole blocking layer 114 is formed. As a material for forming the hole blocking layer 114, a known electron transporting material can be used. In the present example, BAlq is used to form the hole blocking layer 114 with a film thickness of 10 nm by evaporation.

Then, the electron transporting layer 115 is formed. As a material for forming the electron transporting layer 115, a known electron transporting material can be used. In the present example, $Alq_3$ is used to form the electron transporting layer 115 with a film thickness of 20 nm by evaporation.

Then, the electron injecting layer 116 is formed. As a material for forming the electron injecting layer 116, a known electron injecting material can be used. In the present example, calcium fluoride (hereinafter, referred to as $CaF_2$) is used to form the electron injecting layer 116 with a film thickness of 2 nm by evaporation.

After forming the layer 102 including the luminescent material, which is formed by laminating the hole injecting layer 111, the hole transporting layer 112, the light-emitting layer 113, the hole blocking layer 114, the electron transporting layer 115, and the electron injecting layer 116 in this way, a second electrode 103 that functions as a cathode is formed by sputtering or evaporation. In the present example, aluminum (150 nm in film thickness) is formed by evaporation on the layer 102 including the luminescent material to obtain the second electrode 103.

In this way, the light-emitting element using the pyrene derivative according to the present invention is formed.

When a voltage is applied to the formed light-emitting element, blue luminescence was observed at a voltage of 5 V or more, and at an applied voltage of 10 V, blue luminescence with a luminance of 2098 $cd/m^2$ (CIE chromatic coordinated of the luminescence: x=0.169, y=0.162) was observed. The luminous efficiency at the voltage of 10 V was 1.03 cd/A.

EXAMPLE 3

In the present example, a case of using a pyrene derivative according to the present invention as a guest material of a light-emitting layer will be described with reference to FIG. 6. In the present example, structures of a first electrode, a second electrode, a hole injecting layer, a hole transporting layer, a hole blocking layer, an electron transporting layer, and an electron injecting layer are the same as those of Example 1. Accordingly, descriptions thereof are omitted.

Figure 6:
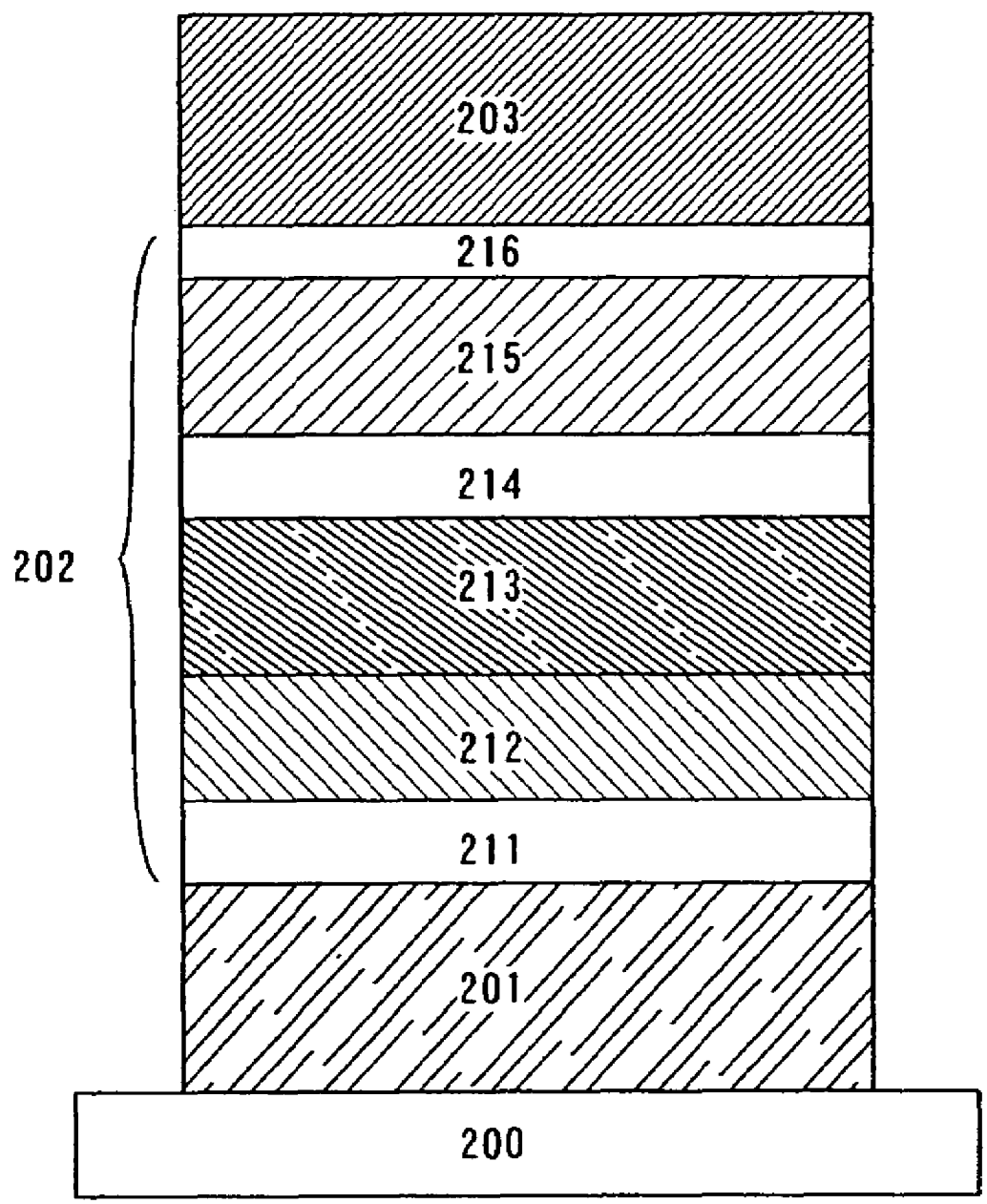
FIG. 6 is a diagram illustrating a structure of a light-emitting element according to the present invention.

Of a layer 202 including a luminescent material to be formed on a first electrode 201, a light-emitting layer 213 to be formed to come in contact with a hole transporting layer 212 as shown in FIG. 6 is formed by using a host material and a guest material that is a pyrene derivative according to the present invention.

Specifically, CBP as the host material and TBiPy as the guest material are used to form the light-emitting layer 213 with a film thickness of 30 nm by co-evaporation. The ratio of the guest material was controlled to be 5 wt %.

Then, a light-emitting element using the pyrene derivative according to the present invention is formed over a substrate 200 by forming a second electrode 203 on the layer 202 including the luminescent material, which is formed by laminating a hole injecting layer 211, the hole transporting layer 212, the light-emitting layer 213, a hole blocking layer 214, an electron transporting layer 215, and an electron injecting layer 216 in this way.

When a voltage is applied to the formed light-emitting element, blue luminescence was observed at a voltage of 7 V or more, and at an applied voltage of 10 V, blue luminescence with a luminance of 74 cd/m$^2$ (CIE chromatic coordinated of the luminescence: x=0.170, y=0.159) was observed. The luminous efficiency at the voltage of 10V was 1.43 cd/A.

The pyrene derivative according to the present invention has a high-efficiency light-emitting property. Therefore, the pyrene derivative can be used as a guest material of a light-emitting layer of a layer including a luminescent material, as shown in the present example. Further, the pyrene derivative according to the present invention has great heat resistance, permits an uniform film to be formed, and is unlikely to undergo crystallization and morphologically stable, which makes it possible to expand the life of a light-emitting element.

COMPARATIVE EXAMPLE 1

In the present comparative example, a case of using 1,3,6,8,-tetra(biphenylyl)pyrene (hereinafter, referred to as t(bp)py) as a guest material of a light-emitting layer will be described with reference to FIG. 7, where the other structures are the same as those of Example 3.

Figure 7:
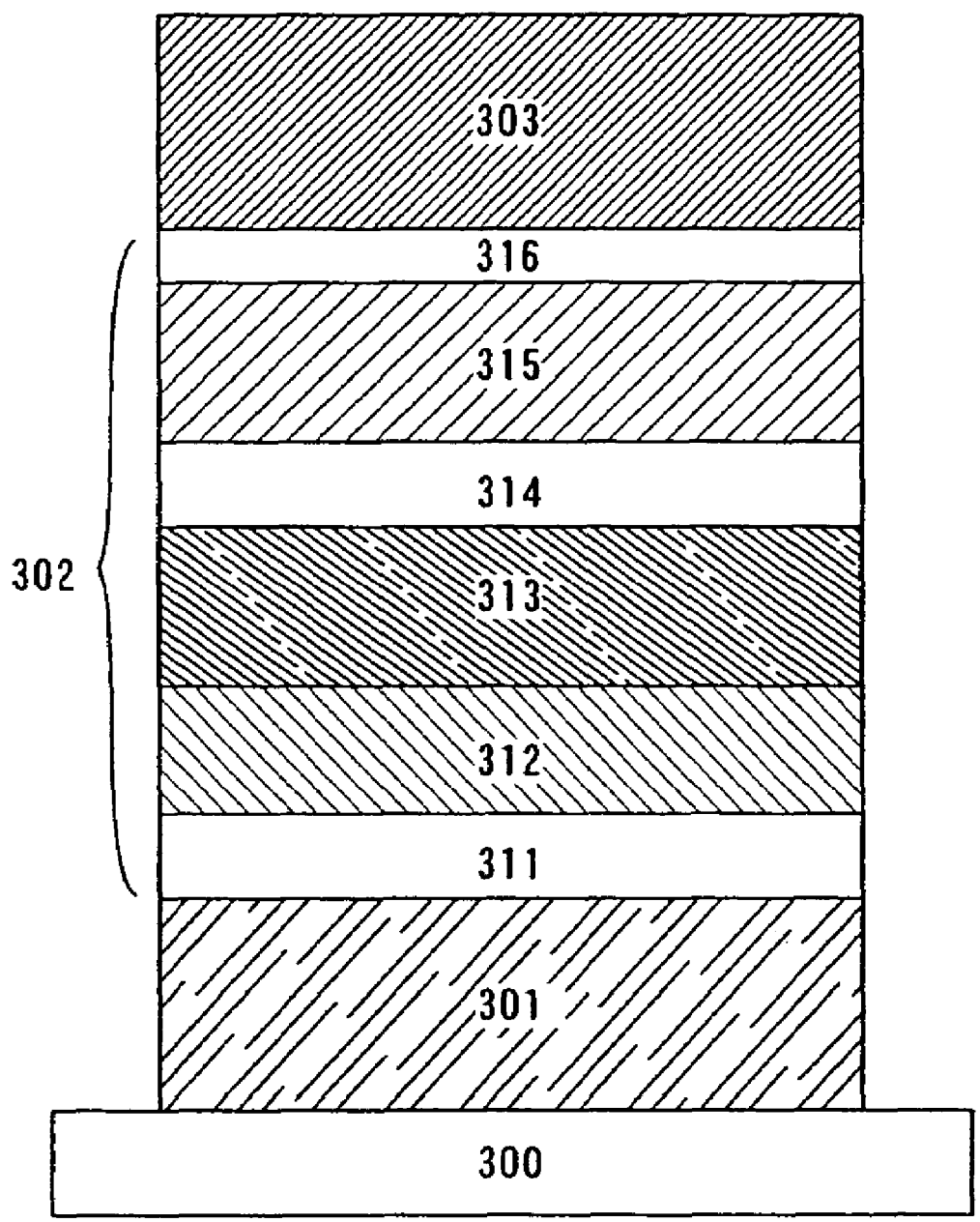
FIG. 7 is a diagram illustrating a structure of a light-emitting element according to the present invention.

Of a layer 302 including a luminescent material to be formed on a first electrode 301, a light-emitting layer 313 to be formed to come in contact with a hole transporting layer 312 as shown in FIG. 7 is formed by using a host material and a guest material that is t(bp)py according to the present comparative example.

Specifically, CBP as the host material and t(bp)py as the guest material are used to form the light-emitting layer 313 with a film thickness of 30 nm by co-evaporation. The ratio of the guest material was controlled to be 5 wt % as in the case of Example 3.

Then, a light-emitting element using t(bp)py is formed over a substrate 300 by forming a second electrode 303 on the layer 302 including the luminescent material, which is formed by laminating a hole injecting layer 311, a hole transporting layer 312, the light-emitting layer 313, a hole blocking layer 314, an electron transporting layer 315, and an electron injecting layer 316 in this way.

When a voltage is applied to the formed light-emitting element, blue luminescence was observed at a voltage of 6 V or more, and at an applied voltage of 10 V, blue luminescence with a luminance of 296 cd/m$^2$ (CIE chromatic coordinated of the luminescence: x=0.154, y=0.140) was observed. The luminous efficiency at the voltage of 10V was 1.03 cd/A, which is somewhat inferior to the case of Example 3 using the structure of the same sort. Further, this light-emitting element was morphologically deteriorated as compared with the cases of Examples 2 and 3.

EXAMPLE 4

In the present example, a light-emitting device that has a light-emitting element according to the present invention in a pixel portion will be described with reference to FIGS. 8A and 8B. FIG. 8A is a top view showing the light-emitting device and FIG. 8B is a cross-sectional view taken along line A–A' in FIG. 8A. Reference numeral 601 indicated by a dotted line denotes a driver circuit portion (a source side driver circuit), reference numeral 602 denotes a pixel portion, and reference numeral 603 denotes a driver circuit portion (a gate side driver circuit). In addition, reference numerals 604 and 605 denote a sealing substrate and a sealing material, respectively. The inside surrounded by the sealing material 605 is a space 607.

A leading wiring 608 is provided for transmitting signals to be input to the source side driver circuit 601 and the gate side driver circuit 603, and receives signals such as a video signal, a clock signal, a start signal, and a reset signal from FPC (Flexible Printed Circuit) 609 that serves as an external input terminal. Though only the FPC is shown in the figure here, a printed wiring board (PWB) may be attached to the FPC. The light-emitting device in the specification includes not only a light-emitting device body but also a state where an FPC or a PWB is attached thereto.

Next, the sectional structure will be explained with reference to FIG. 8B. The driver circuits and the pixel portion are formed over a substrate 610. Here, the source side driver circuit 601 as the driver circuit portion and the pixel portion 602 are shown.

In the source side driver circuit 601, a CMOS circuit is formed of a combination of an n-channel TFT 623 and a p-channel TFT 624. The TFTs forming the driver circuit may be formed of a known CMOS circuit, PMOS circuit, or NMOS circuit. Although the present example shows a driver integrated type in which a driver circuit is formed over a substrate, which is not always necessary, the driver circuit can be formed not over the substrate but outside the substrate.

The pixel portion 602 has a plurality of pixels, each including a switching TFT 611, a current controlling TFT 612, and a first electrode 613 electrically connected to a drain of the controlling TFT. In addition, an insulator 614 is formed to cover an edge of the first electrode 613. Here, a positive photosensitive acrylic resin film is used to form the insulator 614.

Besides, in order to obtain a favorable coverage, the insulator 614 is made to have a top portion or bottom potion formed with a curved surface with a curvature. For example, in the case of using positive photosensitive acrylic as a material for the insulator 614, it is preferable that only a top portion of the insulator 614 has a curved surface with a curvature radius (0.2 μm to 3 μm). In addition, any of a negative photosensitive material that becomes insoluble in an etchant by light and a positive photosensitive material that becomes soluble in an etchant by light can be used as the insulator 614.

On the first electrode 613, a layer 616 including a luminescent material and a second electrode 617 are formed. Here, as a material to be used for the first electrode 613 that functions as an anode, it is preferable to use a material that has a large work function. For example, in addition to single layers such as an ITO film, an indium oxide film including zinc oxide at 2 to 20%, a titanium nitride film, a chromium film, a tungsten film, a Zn film, and a Pt film, laminated structures such as a laminate of a titanium nitride film and a film including aluminum as its main component and a three-layer structure of a titanium nitride film, a film including aluminum as its main component, and a titanium nitride film can be used. When a laminated structure is employed, the wiring has a lower resistance, favorable ohmic contact can be taken, and it is possible to function as an anode.

The layer 616 including the luminescent material is formed by evaporation that uses an evaporation mask or by inkjet. The layer 616 including the luminescent material includes a pyrene derivative according to the present invention. As a material to be used in combination with the pyrene derivative, low molecular weight materials, middle molecular weight materials (including an oligomer and a dendrimer) or high molecular weight materials may be used. In addition, as a material to be used for the layer including the luminescent material, it is often the case that an organic material is used for a single layer or laminate. However, the present invention includes a structure in which an inorganic compound is used for a part of a film including an organic compound.

In addition, as a material to be used for the second electrode (cathode) 617 formed on the layer 616 including the luminescent material, a material that has a small work function (Al, Ag, Li, or Ca; an alloy thereof such as MgAg, MgIn, AlLi, or $CaF_2$; or CaN) may be used. In the case of transmitting light generated in the layer 616 including the luminescent material through the second electrode 617, it is preferable to use a laminate of a metal thin film that has a thinned film thickness and a transparent conductive film (such as ITO, indium oxide including zinc oxide at 2 to 20%, or zinc oxide (ZnO)) as the second electrode (cathode) 617.

Further, the sealing substrate 604 and the substrate 610 are bonded with the sealing material 605 to have a structure where a light-emitting element 618 is provided in the space 607 surrounded by the substrate 610, the sealing substrate 604, and the sealing material 605. The space 607 also includes a structure of filling with the sealing material 605 in addition to a case of filling with an inert gas (such as nitrogen or argon).

It is preferable to use an epoxy resin for the sealing material 605. In addition, it is desirable to use a material that hardly allows permeation of moisture or oxygen. Further, as a material to be used for the sealing substrate 604, a plastic substrate including FRP (Fiberglass-Reinforced Plastics), PVF (polyvinylfluoride), Mylar, polyester, or acrylic can be used besides a glass substrate and a quarts substrate.

In this way, the light-emitting device that has the light-emitting element according to the present invention can be obtained. In the case of this light-emitting device according to the present invention, crystallization in the light-emitting element is suppressed so that stable light emission can be obtained for a long stretch of time.

The light-emitting device shown in the present example can be implemented freely in combination with any of the structures of the light-emitting elements shown in Examples 1 to 3.

EXAMPLE 5

In the present example, various electronic devices completed by using a light-emitting device that has a light-emitting element according to the present invention will be described.

Figure 9A:
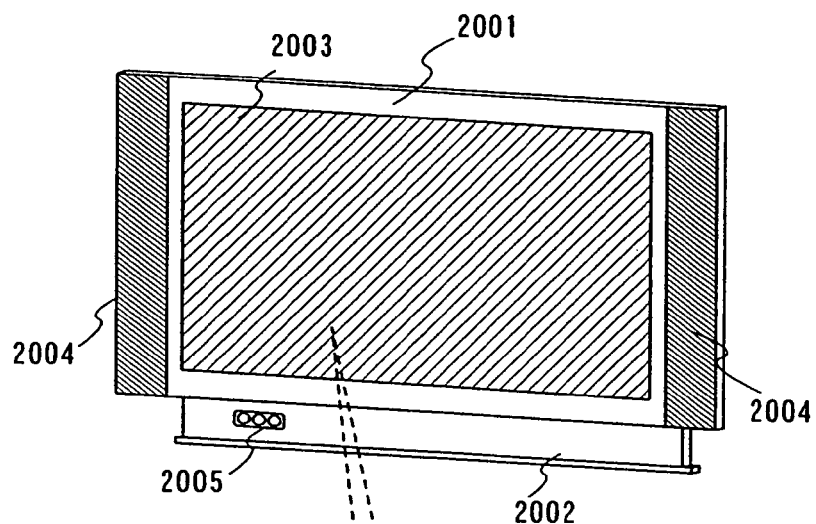
FIGS. 9A to 9C are diagrams illustrating electronic devices.
Figure 9B:
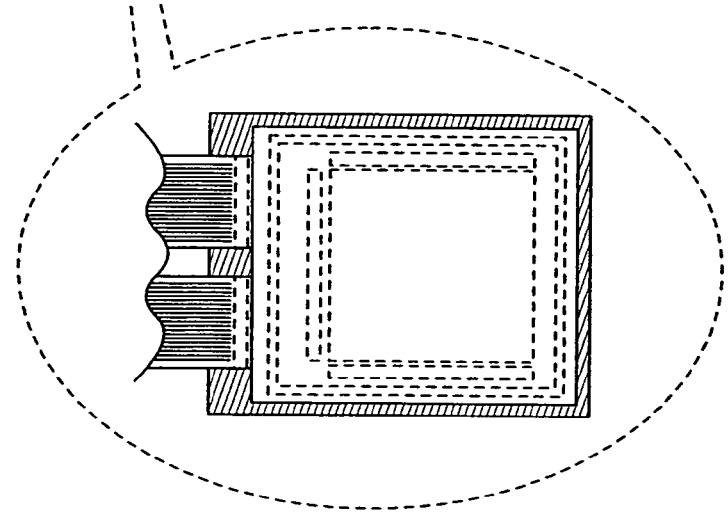
Figure 9C:
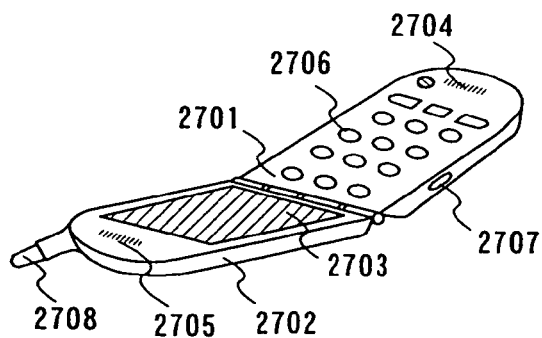

As examples of electronic devices equipped with a light-emitting device formed according to the present invention, a video camera, a digital camera, a goggle-type display (head mount display), a navigation system, a sound reproduction device (such as an in-car audio system or an audio set), a laptop personal computer, a game machine, a personal digital assistant (such as a mobile computer, a cellular phone, a portable game machine, or an electronic book), and an image reproduction device equipped with a recording medium (specifically, a device equipped with a display device, which can reproduce a recording medium such as a digital versatile disc (DVD) and display the image) can be given. FIGS. 9A and 9B show some specific examples of these electronic devices, which will be described.

FIG. 9A is a display device, which includes a frame body 2001, a support 2002, a display portion 2003, a speaker portion 2004, and a video input terminal 2005. A light-emitting device formed according to the present invention is used for the display portion 2003 to manufacture the display device. The display device includes all devices for displaying information such as for a computer, for receiving TV broad casting, and for displaying an advertisement.

FIG. 9B is a cellular phone, which includes a main body 2701, a frame body 2702, a display portion 2703, a voice input portion 2704, a voice output portion 2705, an operation key 2706, an external connection port 2707, and an antenna 2708. A light-emitting device that has a light-emitting element according to the present invention is used for the display portion 2703 to manufacture the cellular phone.

As described above, a light-emitting device that has a light-emitting element according to the present invention is quite widely applied. In addition, since a pyrene derivative according to the present invention is used to form the light-emitting element that is used for the light-emitting device, the light-emitting element has features of a low driving voltage and a long lifetime. Therefore, it is possible to reduce power consumption and extend a lifetime (that is, favorable display images can be obtained for a long time) by applying this light-emitting device to electronic devices in all fields.

Although the present invention has been fully described by way of example with reference to the accompanying drawings, it is to be understood that various changes and modifications will be apparent to those skilled in the art. Therefore, unless such changes and modifications depart from the scope of the present invention hereinafter defined, they should be construed as being included therein.

What is claimed is:

1. A pyrene derivative represented by the following general formula (1),

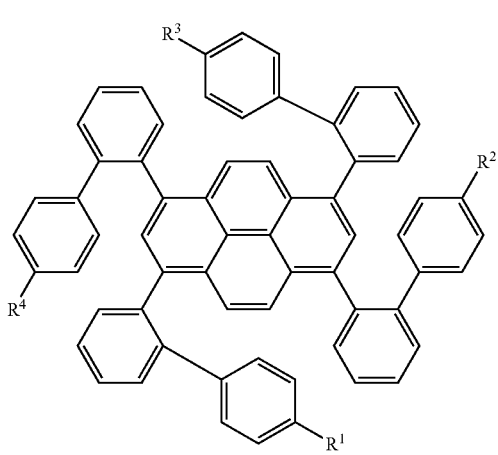

(1)

wherein $R_1$ to $R_4$ are identical or different, and are individually any substituent selected from the group consisting of an alkyl group having 1 to 6 carbon atoms, an alkoxyl group having 1 to 6 carbon atoms, an aryl group, a diarylamino group, and a silyl group having one or more alkyl groups or one or more aryl groups.

2. A light-emitting element comprising a pyrene derivative represented by the following general formula (1) between a pair of electrodes,

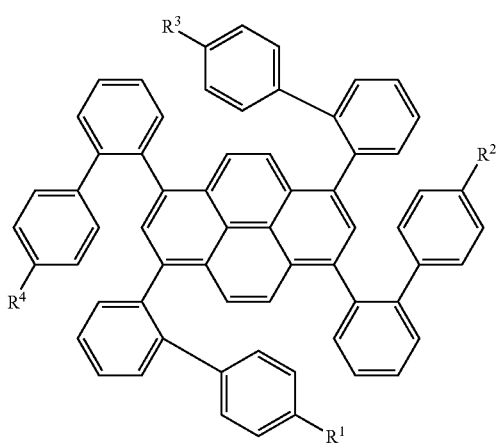

(1)

wherein $R_1$ to $R_4$ are identical or different, and are individually any substituent selected from the group consisting of an alkyl group having 1 to 6 carbon atoms, an alkoxyl group having 1 to 6 carbon atoms, an aryl group, a diarylamino group, and a silyl group having one or more alkyl groups or one or more aryl groups.

3. A light-emitting element comprising a light-emitting layer including a pyrene derivative represented by the following general formula (1) between a pair of electrodes,

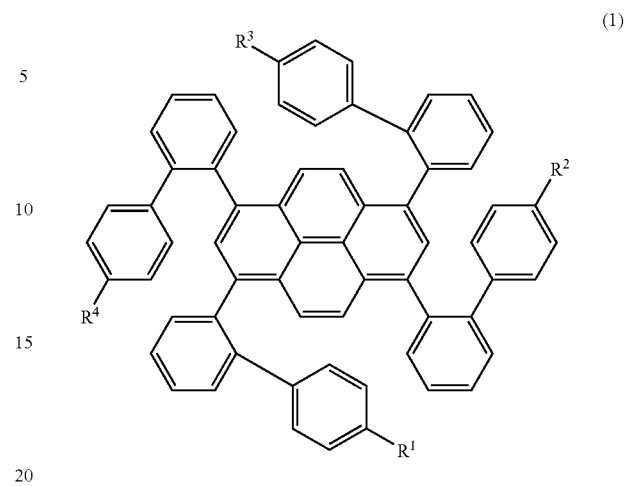

(1)

wherein $R_1$ to $R_4$ are identical or different, and are individually any substituent selected from the group consisting of an alkyl group having 1 to 6 carbon atoms, an alkoxyl group having 1 to 6 carbon atoms, an aryl group, a diarylamino group, and a silyl group having one or more alkyl groups or one or more aryl groups.

4. A light-emitting device comprising the light-emitting element according to claim 1.

5. An electronic device having the light emitting device according to claim 4, wherein the electronic device is selected from the group consisting of a video camera, a digital camera, a goggle-type display, a navigation system, a sound reproduction device, a laptop personal computer, a game machine, a personal digital assistant, a cellular phone, a portable game machine, an electronic book and an image reproduction device equipped with a recording medium.

6. A light-emitting device comprising the light-emitting element according to claim 2.

7. An electronic device having the light emitting device according to claim 6, wherein the electronic device is selected from the group consisting of a video camera, a digital camera, a goggle-type display, a navigation system, a sound reproduction device, a laptop personal computer, a game machine, a personal digital assistant, a cellular phone, a portable game machine, an electronic book and an image reproduction device equipped with a recording medium.

8. A light-emitting device comprising the light-emitting element according to claim 3.

9. An electronic device having the light emitting device according to claim 8, wherein the electronic device is selected from the group consisting of a video camera, a digital camera, a goggle-type display, a navigation system, a sound reproduction device, a laptop personal computer, a game machine, a personal digital assistant, a cellular phone, a portable game machine, an electronic book and an image reproduction device equipped with a recording medium.

10. A light-emitting element according to claim 3, wherein the light-emitting layer comprises a host material including the pyrene derivative and a guest material including a phosphorescent material.

11. A light-emitting element according to claim 10, wherein the phosphorescent material is selected from the group consisting of tris (2-phenylpyridine) iridium and 2,3,7,8,12,13,17,18-octaethyl-21H,23H-porphyrin-platinum, quinacridone, diethyl quinacridone, rubrene, perylene, DPT, Co-6, PMDFB, BTX, ABTX, DOM, and DCJT.

* * * * *